Figure 1:
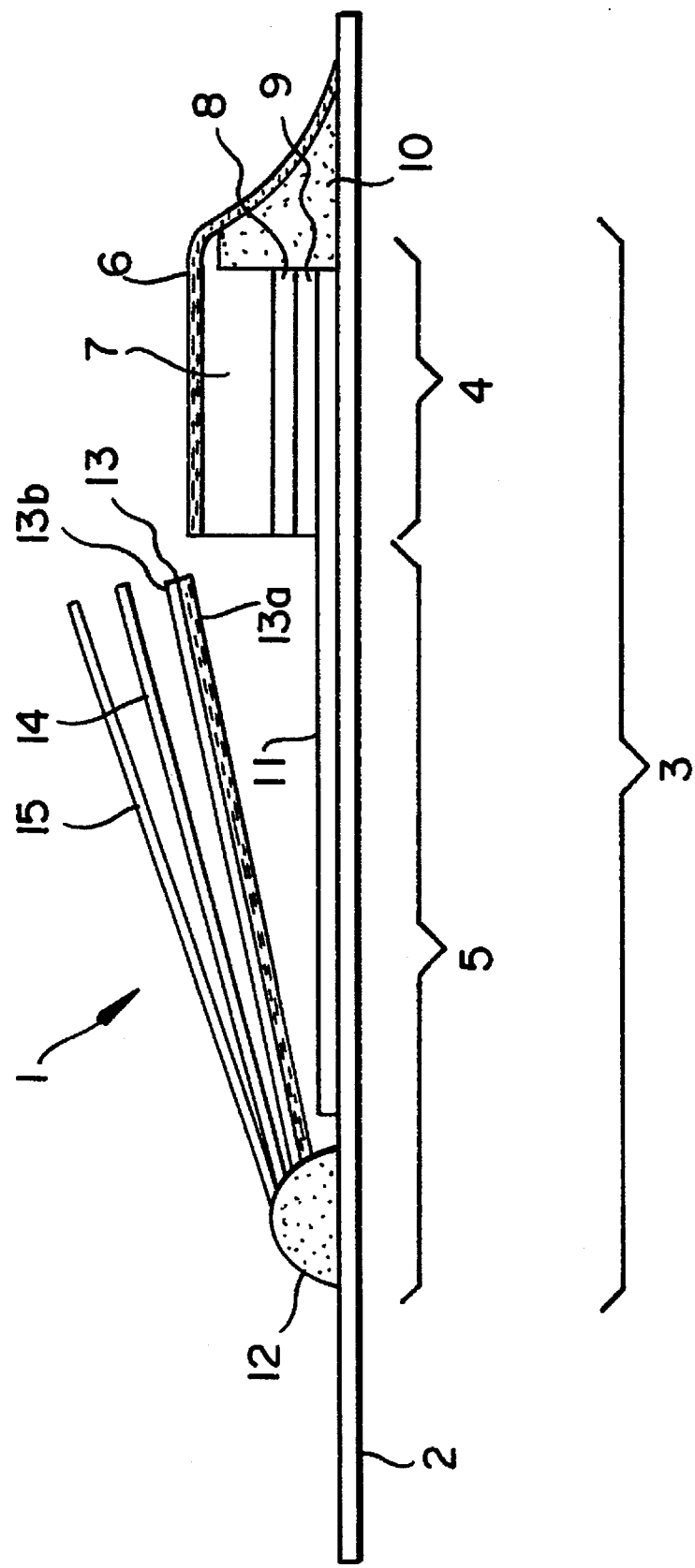

United States Patent [19]

Freitag et al.

[11] Patent Number: 5,460,975

[45] Date of Patent: Oct. 24, 1995

[54] DIPHENYLMETHANE DERIVATIVES, PROCESS FOR THEIR PRODUCTION AND THEIR USE FOR THE DISPLACEMENT OF IODOTHYRONINES FROM PROTEINS WHICH BIND THEM

[75] Inventors: Helmut Freitag, Weinheim; Wolfgang-Reinhold Knappe, Ludwigshafen; Heino Eikmeier, Lorsch; Wolfgang Weckerle, Grunstadt, all of Germany

[73] Assignee: Boehringer Mannheim GmbH, Mannheim, Germany

[21] Appl. No.: 89,296

[22] Filed: Jul. 7, 1993

Related U.S. Application Data

[63] Continuation of Ser. No. 824,281, Jan. 23, 1992, abandoned.

[30] Foreign Application Priority Data

Feb. 2, 1991 [DE] Germany ............... 41 03 167.9

[51] Int. Cl.[6] ............... G01N 33/78; G01N 33/537
[52] U.S. Cl. ............... 436/500; 435/7.9
[58] Field of Search ............... 436/500; 435/7.9

[56] References Cited

U.S. PATENT DOCUMENTS

| | | | |
|---|---|---|---|
| 3,711,096 | 10/1975 | Chope | 436/500 |
| 3,928,553 | 12/1975 | Holkinder | 436/500 |
| 4,233,402 | 10/1980 | Maggio et al. | 436/500 |
| 4,256,834 | 3/1981 | Zuk et al. | 436/500 |
| 4,261,968 | 4/1981 | Ullman et al. | 436/500 |
| 4,468,467 | 8/1984 | Atkinson et al. | 436/500 |
| 4,472,498 | 9/1984 | Masuda et al. | 436/500 |
| 4,622,293 | 11/1986 | Ellis et al. | 436/500 |
| 4,741,897 | 5/1988 | Andrews et al. | 436/500 |
| 4,771,008 | 8/1988 | Miara et al. | 436/500 |
| 4,843,018 | 6/1989 | Berger et al. | 436/500 |
| 4,876,067 | 10/1989 | Deneke et al. | 422/56 |
| 5,063,165 | 11/1991 | Hu et al. | 436/500 |
| 5,244,786 | 9/1993 | Picone et al. | 436/500 |

FOREIGN PATENT DOCUMENTS 0133464  2/1985  European Pat. Off. .

OTHER PUBLICATIONS

Tijssen et al, "Practice & Theory of Immuno Assays", Elsevier, NY, N.Y., 1985. Pp. 9–20 & 329–349.

WO–A–9106589, International Publication date May 16, 1991.

*Primary Examiner*—Michael P. Woodward
*Attorney, Agent, or Firm*—Nikaido, Marmelstein, Murray & Oram

[57] ABSTRACT

The present invention concerns compounds having the general formula I

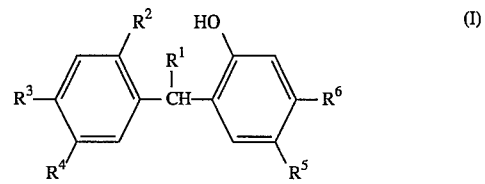

in which $R^1$ denotes hydrogen or hydroxy, $R^2$ denotes hydrogen or hydroxy, $R^3$ denotes hydrogen or alkoxy, $R^4$ denotes hydrogen, $CO_2H$, $SO_3H$, $PO_3H_2$ or a salt of the corresponding acid, $R^5$ denotes $CO_2H$, $SO_3H$, $PO_3H_2$ or a salt of the corresponding acid and $R^6$ denotes alkoxy, their use for displacing iodothyronines from proteins binding them, as well as a method and reagent for the determination of iodothyronine in which such compounds are used.

20 Claims, 1 Drawing Sheet

DIPHENYLMETHANE DERIVATIVES, PROCESS FOR THEIR PRODUCTION AND THEIR USE FOR THE DISPLACEMENT OF IODOTHYRONINES FROM PROTEINS WHICH BIND THEM

This application is a continuation of application Ser. No. 07/824,281 filed Jan. 23, 1992, now abandoned.

The invention concerns diphenylmethane derivatives having the general formula I

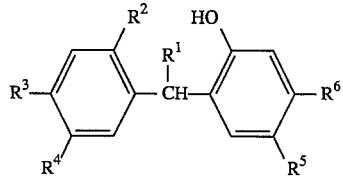

in which $R^1$ and $R^2$ are the same or different and denote hydrogen or hydroxy, $R^3$ denotes hydrogen or alkoxy, $R^4$ denotes hydrogen, $CO_2H$, $SO_3H$, $PO_3H_2$ or a salt of the corresponding acid, $R^5$ denotes $CO_2H$, $SO_3H$, $PO_3H_2$ or a salt of the corresponding acid and $R^6$ denotes alkoxy as well as a process for the production of such compounds.

The invention concerns in particular the use of such compounds to displace iodothyronines from proteins which bind them, especially in a method for the determination of an iodothyronine in the presence of an iodothyronine-binding protein in a liquid sample by addition of a substance which displaces and releases protein-bound iodothyronine and determination of the total iodothyronine in the sample, in particular by means of an immunological method. In addition the invention concerns the use of the compounds according to the present invention in a corresponding reagent for the determination of iodothyronine.

Iodothyronines within the sense of the present invention are in particular those which are of interest in clinical diagnosis. Such iodothyronines are in particular 3,5,3',5'-tetraiodothyronine (thyroxine; T4), 3,5,3'-triiodothyronine (T3), 3,3', 5'-triiodothyronine and 3,3'-diiodothyronine. The quantitative determination of the concentration of T4 and/or T3 in blood or in samples derived from blood such as plasma or serum plays a very important role in the examination of thyroid function. A large portion of the iodothyronine present in blood, plasma or serum is bound to protein. Examples of such iodothyronine-binding proteins are albumin, thyroxine-binding prealbumin and above all "thyroxine-binding globulin" (TBG).

In order to determine the total content of iodothyronine in a blood sample it is necessary in many methods to dissociate protein-bound iodothyronine from its respective carrier protein in order to then be able to determine the iodothyronine present in a free form. In order to release protein-bound iodothyronine it is customary to add so-called "displacing reagents" which displace iodothyronine from its respective binding site on the protein and which themselves bind to the protein.

Such displacing reagents are known for example from the European Patent Application No. 0 078 477 and 0 133 464.

EP-A 0 078 477 describes substances having a displacing effect which have the general formula $Z_1$-Y-$Z_2$, in which $Z_1$ and $Z_2$ represent phenyl groups which can be substituted by halogen, alkyl and/or alkoxy and one of these phenyl rings carries a carboxylic acid or sulfonic acid residue. Y can be oxygen, imine, sulphur, methylene or carbonyl. However, phenylacetic acid derivatives which are substituted by chlorine are preferred.

In EP-A 0 133 464 2-hydroxy-4-methoxybenzophenone-5-sulfonic acid and salts of this acid are described as being particularly advantageous for displacing iodothyronine from protein which binds it.

The release of iodothyronine which was previously bound to protein is followed by a determination of free iodothyronine in the sample. Immunological methods are usually used for this. In such immunological methods iodothyronine is bound to its respective antibodies. The extent of iodothyronine binding to the antibodies, i.e. how much iodothyronine has been bound to the antibody, is determined by immunological test reagents which contain markers allowing a quantitative determination of the iodothyronine content of the sample to be examined. Potential markers are enzymes which catalyze certain reactions and which indicate how much iodothyronine is present in the sample to be determined by the extent of such an enzymatic reaction.

In order to reliably determine the total content of iodothyronine in the sample it is necessary that the displacing reagent used neither influences the immunochemical reaction, i.e. the reaction of the specific antibody with iodothyronine, nor the activity of the enzyme marker. However, previously known substances for displacing iodothyronine from its respective carrier proteins either show a lack of displacing activity or they interfere with the immunological determination of iodothyronine by impairing the iodothyronine-antibody reaction or the activity of an enzyme marker in those concentrations in which they have a displacing effect.

The object of the present invention was therefore to provide compounds which displace iodothyronine as much as possible from its respective binding proteins and which in addition to not impair immunological test reactions for iodothyronine especially enzyme-immunoassays.

This object is achieved by the subject matter of the present invention as characterized in the patent claims.

The invention concerns compounds having the general formula I

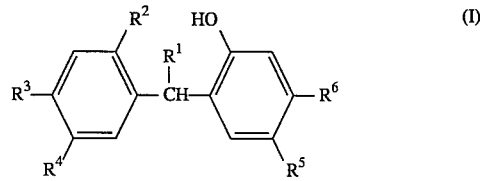

in which $R^1$ and $R^2$ are the same or different and denote hydrogen or hydroxy, $R^3$ denotes hydrogen or alkoxy, $R^4$ denotes hydrogen, $CO_2H$, $SO_3H$, $PO_3H_2$ or a salt of the corresponding acid, $R^5$ denotes $CO_2H$, $SO_3H$, $PO_3H_2$ or a salt of the corresponding acid and $R^6$ denotes alkoxy.

In the definition of the compounds having the general formula I alkoxy residues are in particular those with 1 to 6 carbon atoms. Particularly preferred are alkoxy residues with 1 to 3 carbon atoms. The methoxy residue is especially preferred.

A salt of one of the acid residues given as a possible meaning for the residues $R^4$ and $R^5$ is understood to in particular include alkali, alkaline-earth and ammonium salts. Alkali salts are understood as lithium, sodium, potassium, rubidium and caesium salts, whereby lithium, sodium and potassium salts and above all sodium and potassium salts are preferred and sodium salts are especially preferred. Alkaline-earth salts are those of beryllium, magnesium, calcium, strontium or barium. Magnesium and calcium salts are preferred, whereby calcium salts are particularly preferred. Salts of the unsubstituted ammonium ion, $NH_4+$, may be used as ammonium salts. It is, however, also possible to use those ammonium salts in which the ammonium ion is substituted by 1 to 4 alkyl, aryl or aralkyl residues. In this case "alkyl" denotes a straight-chained or branched alkyl residue with 1 to 6, preferably 1 to 4 carbon atoms. Examples are the methyl, ethyl, propyl, isobutyl or tert. butyl group. Alkyl residues which are preferred as substituents of the ammonium ion are methyl, ethyl and n-propyl. "Aryl" denotes a carbon aromatic or heteroaromatic residue, preferably one which has 6 to 10 ring atoms, in particular a phenyl or naphthyl group which can in addition be substituted by alkyl, alkoxy or/and halogen. In this case halogen can represent the residues fluorine, chlorine, bromine and iodine. Fluorine and chlorine are preferred. "Alkyl" and "alkoxy" have the meanings given previously. A particularly preferred aryl residue in substituted ammonium ions is the phenyl residue. An "aralkyl", residue denotes a residue in which an alkyl group as defined above is substituted by an aryl residue specified above. The benzyl group is preferred. Especially preferred salts of the compounds according to the present invention having the general formula I are alkali salts having the aforementioned meaning.

Preferred compounds having the general formula I are those in which at least one of the possible acid residues $R^4$ or $R^5$ is a sulfonic acid group or a salt of such an acid group.

The object according to the present invention is achieved particularly well by compounds having the general formula I,
in which
$R^1$ denotes hydrogen or hydroxy,
$R^2$, $R^3$ and $R^4$ denote hydrogen
$R^5$ denotes $SO_3H$ or a corresponding salt and
$R^6$ denotes alkoxy
as well as by those compounds having the general formula in which
$R^1$ denotes hydrogen or hydroxy,
$R^2$ denotes hydroxy,
$R^3$ denotes alkoxy,
$R^4$ denotes $SO_3H$ or a corresponding salt,
$R^5$ denotes $SO_3H$ or a corresponding salt and
$R^6$ denotes alkoxy.

Of the compounds mentioned as being preferred those in which $R^1$ denotes hydrogen can be used most advantageously. Particularly suitable examples of such diphenylmethane derivatives are in particular 2-hydroxy-4-methoxy-diphenylmethane-5-sulfonic acid and corresponding salts as well as 2,2'-dihydroxy-4,4'-dimethoxydiphenylmethane-5, 5'-disulfonic acid and its corresponding salts. In particular the latter acid and its salts, especially the disodium salt, is exceptionally suitable according to the present invention.

The compounds according to the present invention are novel. A particular feature is that they are readily soluble in water and aqueous media such as buffer solutions and are able to readily displace iodothyronines, in particular thyroxine, from proteins which bind them especially from TBG. A special characteristic of these compounds is that while having a very good displacing effect their potential for interference in immunological test reactions is substantially reduced compared with previously known prior art. This relates in particular to immunological reactions at the stage of the iodothyronine-antibody binding reaction as well as to enzymatic reactions of enzyme markers with corresponding substrates.

The invention also concerns a process for the production of the compounds according to the present invention. Compounds having the general formula I are preferably produced by reducing compounds having the general formula II

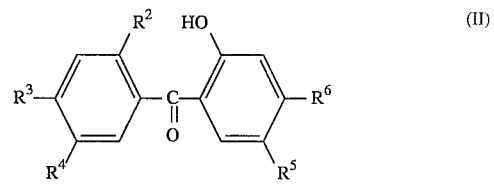

in which
$R^2$ denotes hydrogen or hydroxy,
$R^3$ denotes hydrogen or alkoxy,
$R^4$ denotes hydrogen, $CO_2H$, $SO_3H$, $PO_3H_2$ or a salt of the corresponding acid,
$R^5$ denotes $CO_2H$, $SO_3H$, $PO_3H_2$ or a salt of the corresponding acid and
$R^6$ denotes alkoxy.

In this case the residues have the same meanings as stated for compounds of the general formula I.

Selection of appropriate reducing conditions can be used to regulate the meaning of $R^1$ in compounds having the general formula I. Thus when a ketone having the general formula II is reacted with sodium cyanoborohydride under acidic conditions, a compound having the general formula I is obtained in which $R^1$ denotes hydrogen. Such a reaction is preferably carried out in an aqueous medium at pH 2 to 4.

The same result is also obtained if the ketone having the general formula II is hydrogenated with hydrogen in the presence of palladium on carbon. This is preferably carried out while stirring for several hours in a hydrogen atmosphere.

However, if a ketone having the general formula II is hydrogenated with hydrogen in the presence of platinum(IV)oxide in this case a compound having the general formula I in which $R^1$ denotes hydroxy is obtained. For this it is also preferable to stir for several hours in a hydrogen atmosphere.

The process according to the present invention is preferably carried out at temperatures between 10° and 40° C., particularly preferably at room temperature.

In addition the invention also concerns the use of compounds having the general formula I to displace iodothyronine from proteins which bind it, in particular in a method and reagent for the determination of iodothyronine in the presence of iodothyronine-binding protein.

The method according to the present invention for the determination of an iodothyronine in the presence of iodothyronine-binding protein in a liquid sample by addition of a substance which displaces and releases protein-bound iodothyronine and determination of the total iodothyronine in the sample is characterized in that a compound having the general formula I is added to the sample as the displacing substance. The concentration necessary to displace iodothyronine from protein which binds it is of course dependent on the amount of binding protein in the sample. It has been found in practice for human samples, in particular blood, plasma or serum, that when the concentration of the substance having the general formula I according to the present invention is adjusted to at least 6 mmol/l, iodothyronine in the sample to be examined and in particular T4, is almost completely displaced from iodothyronine-binding protein in the sample, in particular from "thyroxine-binding globulin" (TBG). A concentration of 8 to 30 mmol/l has proven to be particularly preferable. The lower limits of this concentration range are those which are necessary to achieve an almost complete displacement of iodothyronine from its respective binding protein in the sample. The upper limits of the concentration range are mostly determined by economical considerations. Using more displacing reagent than necessary leads to no further displacing effect. It has been shown in practice that the concentration range stated as being preferred is optimal for the determination of iodothyronine concentrations occurring in vivo. However, apart from these considerations it is up to the discretion of one skilled in the art to determine the optimal concentration of a substance having the general formula I in any individual case.

In order to determine the total iodothyronine content in a sample the displacing reaction described above is followed by a test for iodothyronine in the sample. This can be carried out according to previously known methods. Usually immunological methods of determination are used. In this context immunological methods of determination or immunoassays are understood as those methods which are based on an interaction between antigen or hapten and antibody. Antibodies can be used in the form of whole antibodies (polyclonal or monoclonal antibodies) or fragments having a similar activity, for example Fab.

In order to carry out immunoassays either the antibody used or a compound analogous to the substance to be determined must be labelled in a detectable form. According to the present invention compounds having the general formula I are particularly suitable for use in such methods in which enzymes are used as markers. Such methods of determination are known as enzyme-immunoassays (see for example M. Oellerich, J. Clin. Chem. Clin. Biochem. 22., 895–904 (1984)). Since the concentrations of the compounds according to the present invention necessary to displace iodothyronine from proteins which bind it neither substantially interfere with the binding of iodothyronine to its respective antibody nor with the activity of enzymes used for enzyme-immunoassays, the provision of the compounds according to the present invention provides an especially beneficial method for the determination of total iodothyronine by means of enzyme-immunoassays.

The markers used in enzyme-immunoassays are in particular peroxidase, alkaline phosphatase or β-D-galactosidase. The use of compounds having the general formula I according to the present invention for the displacement of iodothyronine from proteins which bind it have proven to be advantageous especially when using β-D-galactosidase as the enzyme marker in enzyme-immunoassays.

According to the present invention enzyme-immunoassays which are based on the IEMA method, so-called "immuno-enzymometric assays", are especially preferred. In this method enzyme-labelled antibody is added in excess to the sample to be examined. Free iodothyronine in the sample to be examined binds to this antibody. Excess free labelled antibody is then separated in a further step in which iodothyronine immobilized on a solid phase is added in excess and as a result the free antibody is immobilized on the solid phase. The solid phase is then separated from the liquid phase. The amount of iodothyronine to be determined in the examined sample is determined on the basis of the enzyme activity present either in the liquid phase or on the solid phase which can be assayed by means of an appropriate enzyme substrate.

The present invention also concerns a reagent for carrying out the method according to the present invention for the determination of iodothyronine in the presence of iodothyronine-binding protein in a liquid sample. Such a reagent must contain a substance which is suitable for the displacement of iodothyronine from protein which binds it and in addition an agent which generates a signal with the free unbound iodothyronine which represents a measure of the amount of iodothyronine in the sample. According to the present invention such a reagent is characterized in that it contains a compound having the general formula I as the displacing substance. In principle any agent which is suitable for the purpose can be used as the agent for the determination of free unbound iodothyronine. Those substances are preferably used as components of the agent for the determination of free unbound iodothyronine in the reagent according to the present invention which are necessary for an immunoassay, preferably an enzyme-immunoassay. In order to carry out an IEMA test, which is particularly preferred according to the present invention, the reagent must contain enzyme-labelled antibody, iodothyronine immobilized on a carrier and an appropriate substrate for the enzyme marker whose enzymatic conversion leads to a signal, for example formation of colour or change in colour, which is a measure of the amount of iodothyronine in the sample.

The reagent according to the present invention preferably contains a buffer substance which sets the pH in the sample to be examined to that at which the displacement reaction by means of the substance having the general formula I according to the present invention and also the determination of free unbound iodothyronine can be carried out. For this purpose it is particularly preferable to use a buffer substance which sets a pH value between 6 and 8.

The reagent according to the present invention can contain the substance which displaces iodothyronine from protein which binds it in a mixture together with the agent which generates a signal with free unbound iodothyronine, which is a measure of the amount of iodothyronine in the sample to be examined. However, it is preferred that the displacing substance and the agent for carrying out the determination reaction are kept spatially separated from one another.

The reagent according to the present invention can be present as a solution. Thus for example according to the details set forth above the substance having the general formula I can be present in a common medium together with the agent for the determination of free unbound iodothyronine. The reagent according to the present invention can, however, also consist of several separate solutions which each contain individual reagent components. The displacing substance is preferably separate from the agent for the determination of free unbound iodothyronine. The solvents which are preferably used are those which are suitable for dissolving the compounds having the general formula I according to the present invention as well as for incorporating the components of the agent for the determination of free unbound iodothyronine. Above all aqueous solvents are suitable and especially preferably buffer solutions.

A reagent according to the present invention can also contain the substance for the displacement of iodothyronine from protein which binds it in or on a solid inert carrier while the agent for the determination of free unbound iodothyronine is present as a solution. The opposite situation is also possible.

In an especially preferred embodiment of the reagent according to the present invention it is present entirely bound to a carrier. For example a test carrier as shown in FIG. 1 is suitable for this. Such a test carrier is described in detail in EP-A-0 318 777. The test carrier 1 shown in FIG. 1 has the basic form of a test strip. It is a high-quality analysis system especially for carrying out immunological determinations. The entire test region, labelled 3, is located on a base layer 2 and extends over only part of the length of base layer 2. The test region 3 can be subdivided into a sample application zone 4 and into a test zone 5. In the sample application zone 4 one can see from top to bottom a covering net 6, a layer for separating erythrocytes 7 and two reagent layers 8 and 9 which are attached to the base layer 2 with a strip of hot-melting adhesive 10.

A liquid transport layer 11 comprising an absorptive material which is also attached with the hot-melting adhesive strip 10, extends beyond the sample application zone 4 into the test zone 5. Three layers are located above that region of the liquid transport layer which is not covered by the layers 6 to 9 and these are mounted on the base layer 2 with a strip of hot-melting adhesive 12 in such a way that in the absence of external pressure they stick out at an angle to the base layer and do not touch it. These layers are a test layer 13 with immobilized analyte or analyte analogue, a third reagent layer 14 and a covering foil 15.

The preferred test carrier shown here is especially suitable for carrying out immunological determinations which are based on the so-called IEMA technique. If iodothyronine (for example T4) is to be determined in a sample then the analysis using the test carrier shown in FIG. 1 is carried out as follows:

A drop of blood (about 30 µl) is applied above the erythrocyte separation layer to the covering net 6 and penetrates the erythrocyte separation layer 7 which can for example be constructed according to the U.S. Pat. No. 4,477,575. The serum obtained in this way penetrates through layer 8 into layer 9. Layer 8 contains a compound having the general formula I according to the present invention so that here the sample derived from the blood takes up the substance which displaces iodothyronine from its respective binding proteins and thus allows a determination of the total iodothyronine in the sample. Layer 9 contains an enzymatically labelled antibody for iodothyronine which is in excess over the maximum iodothyronine concentration in the sample. This antibody-enzyme conjugate (ABE) is dissolved by the penetrating serum. In this process complexes form between the AbE and iodothyronine which are denoted I-AbE. Since the AbE is present in excess, free conjugate AbE remains when the equilibrium has been reached. The object of layer 13 is to remove AbE from this by immunological binding which would otherwise interfere with the following test. It is therefore also denoted immunological separation layer. It contains iodothyronine or an iodothyronine analogue in carrier-bound form whereby immobilization on the carrier is carried out with the aid of inorganic carrier particles such as those described for example in EP-A-0 318 777. It is expedient to use $SiO_2$ particles as the carrier particles such as those which are for example supplied as silica gels for chromatographic purposes. However, the use of titanium oxide is especially preferred.

After a predetermined incubation period in which bound iodothyronine is displaced from its respective binding proteins in the sample and an equilibrium has been established between free unbound iodothyronine and ABE, pressure is applied to the layers 13 to 15 from above. This can be carried out manually or—as described for example in EP-A-O 129 220—mechanically with the aid of an instrument component. The downward pressure brings the immunological separation layer 13 into contact with the liquid transport layer 11 and the components which are present there penetrate into the layer 13. In this process the non-complexed AbE couple with the immobilized iodothyronine while the I-AbE complexes can penetrate further without hindrance.

The reagent layer 14 contains a chromogenic substrate for the enzyme marker. When the liquid reaches the substrate the enzyme in the free I-AbE complexes catalyzes the colour reaction of the substrate. The rate of change in colour is therefore a measure of the amount of free I-AbE complexes which reach the reagent layer 14. This is in turn a measure of the amount of iodothyronine in the sample.

Possible materials for the individual layers of the test carrier according to FIG. 1 can be taken from EP-A-0 318 777.

In the following the invention is elucidated further by examples.

EXAMPLE 1

2-hydroxy-4-methoxydiphenylmethane-5-sulfonic acid sodium salt

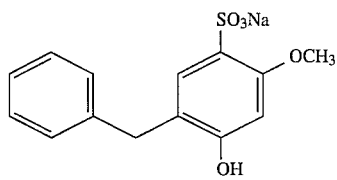

a) Sodium cyanoborohydride (60 g, 950 mMol) in water (700 ml) is added to 2-hydroxy-4-methoxybenzo-phenone-5-sulfonic acid (Uvinul MS-40 BASF Company, Ludwigshafen/Rhein, Germany; 74 g, 240 mMol) in water (1200 ml) and stirred at room temperature. The pH of the solution is kept at 3.5 over 4 hours by the continuous addition of 2N hydrochloric acid and subsequently it is adjusted to pH 2 by further addition of hydrochloric acid. Afterwards air is conducted through the solution which is heated to 50° C. for the duration of 6 hours in order to completely remove hydrogen cyanide liberated during the reaction. The solution is concentrated in a vacuum and the residue is digested with methanol. The undissolved portion (sodium chloride) is aspirated and the filtrate is poured into ether in order to precipitate the product. The title compound is obtained in pure form by dissolving again in warm ethanol and precipitating in diethyl ether.: yield 70 g (92%); m.p. >270° C.; $R_f$ 0.3 [silica gel; mobile solvent: isopropanol/n-butylacetate/water/25% aqueous ammonia=10:6:3:1 (v/v/v/v )].

b) As an alternative the title compound can also be produced as follows:
2-hydroxy-4-methoxybenzophenone-5-sulfonic acid (Uvinul MS-40 BASF Company, Ludwigshafen/ Rhein, Germany; 5 g, 16 mMol) in methanol (500 ml) is stirred for 6 hours at room temperature under a hydrogen atmosphere in the presence of palladium/ carbon (10%, 1 g). After aspirating the catalyzer, 1N methanolic sodium methylate solution is added, the solution is concentrated in a vacuum (residual volume ca. 100 ml) and diethyl ether (1000 ml) is added in order to precipitate the product; yield 4 g (79%); m.p.>270° C.; $R_f$ 0.3 [silica gel; mobile solvent: isopropanol/n-butylacetate/water/25% aqueous ammonia=10:6:3:1 (v/v/v/v)].

EXAMPLE 2

2,2'-dihydroxy-4,4'-dimethoxydiphenylmethane-5,5'-disulfonic acid disodium salt

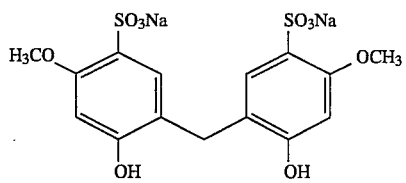

2,2'-dihydroxy-4,4'-dimethoxybenzophenone-5,5'-disulfonic acid disodium salt (Uvinul DS-49 BASF Company, Ludwigshafen/Rhein, Germany; 144 g, 0.3 mMol) is deoxygenated with sodium cyanoborohydride (57 g, 900 mMol) in water (3000 ml) at room temperature for 8 hours in an analogous manner to that described in Example 1 during which the pH is kept at 3.5 by the continuous addition of 2N hydrochloric acid (total consumption ca. 250 ml). It is processed as described previously to yield the desired compound; yield: 103 g (74%); m.p.>260° C.; $R_f$ 0.75 [HPTLC-RP 18, E. Merck Company, Darmstadt, Germany; mobile agent: ethanol/water =7:3 (v/v)].

EXAMPLE 3

2-hydroxy-4'-methoxydiphenylcarbinol-5-sulfonic acid ammonium salt

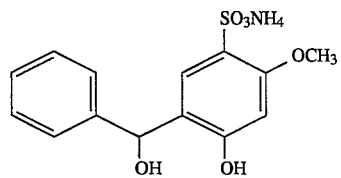

Pyridine (4 g, 50 mMol) and $PtO_2$ (3 g) are added to 2-hydroxy-4-methoxybenzophenone-5-sulfonic acid (Uvinul MS-40 BASF Company, Ludwigshafen/Rhein, Germany; 15.4 g, 50 mMol) in methanol (800 ml) and stirred for 24 hours at room temperature under a hydrogen atmosphere. After filtering off the catalyzer and concentrating the filtrate the residue is purified by column chromatography on silica gel [mobile solvent: methylene chloride/methylethylketone/methanol/concentrated aqueous ammonia=5:1:2:0.3 (v/v/v/v)]. Concentrating the fraction with a $R_f$ of 0.12 yields the title compound; yield 9.5 g (58%); m.p. 211° C.

EXAMPLE 4

Method for the determination of total thyroxine (T4)
A) Test procedure
  The following are pipetted successively into a centrifuge tube:
    80 μl serum with 0–20 μg/dl T4
    20 μl displacing reagent solution in buffer (0–30 mM)

Then mix for 2 minutes. Subsequently
  25 μl (anti-T4 antibody)-β-galactosidase conjugate in buffer (40 U/ml) is added to this mixture. The buffer is the same as for the displacing reagent. It is mixed again for 2 minutes. Then
  20 μl titanium dioxide-T4 suspension in buffer (50%) is added. The titaniumdioxide-T4 suspension is prepared as described in EP-A-0 318 777 (example 1.2). After mixing again for two minutes the solid components are removed by centrifugation and
  20 μl of the supernatant is added to
  750 82 l chlorophenol red-galactoside in buffer (1 mM). Chlorophenol red-galactoside is prepared according to EP-A 0 146 866.
After a short mixing the absorbance change/minute is measured at 578 nm.

In each case the buffer used is an aqueous solution (pH=7.0) of the following substances:

| | |
|---|---|
| $KH_2PO_4$ | 10 mM |
| $MgCl_2$ | 5 mM |
| NaCl | 25 mM |

B) Results a) Table 1 shows the dependence of the measured signal (absorbance change per minute) on the concentration of the displacing reagent (DR) used for the substances 2-hydroxy-4-methoxydiphenylmethane-5-sulfonic acid (sodium salt) (α) and 2,2'-dihydroxy-4,4'-dimethoxydiphenylmethane-5,5'-disulfonic acid (disodium salt) (β). As a comparison the measured value for a TBG-free serum (measurement without DR) with an identical T4 concentration (in this case: 5.0 μg/dl in the test mixture) is shown.

TABLE 1

| 5.0 μg/dl T4 in the total test mixture | | | |
|---|---|---|---|
| DR concentration in the mixture | Change in absorbance/minute for the substance | | TBG-free |
| (mM) | α | β | control |
| 0 | 0.13 | 0.20 | 0.63 |
| 2 | 0.35 | 0.45 | |
| 4 | 0.50 | 0.60 | |
| 6 | 0.57 | 0.65 | |
| 8 | 0.60 | 0.66 | |
| 10 | 0.65 | 0.66 | |

The displacing effect of substance β reaches completion above a concentration of ca. 6 mM.
Substance α leads to the "correct" measurement signal at a concentration between 8 and 10 mM in the mixture.

b) Table 2 shows the experiment carried out using various T4 concentrations in the mixture with substance β.

TABLE 2

| Substance β at different T4 concentrations | | | | |
|---|---|---|---|---|
| DR concentration | Change in absorbance/minute at a T4 concentration in the mixture (μg/dl) | | | |
| in the mixture (mM) | 0.6 | 5.0 | 9.0 | 15.0 |
| 0 | 0.15 | 0.18 | 0.21 | 0.35 |

TABLE 2-continued

Substance β at different T4 concentrations

| DR concentration in the mixture (mM) | Change in absorbance/minute at a T4 concentration in the mixture (μg/dl) | | | |
|---|---|---|---|---|
| | 0.6 | 5.0 | 9.0 | 15.0 |
| 2 | 0.20 | 0.40 | 0.65 | 0.92 |
| 4 | 0.24 | 0.54 | 0.83 | 1.10 |
| 6 | 0.25 | 0.61 | 0.89 | 1.22 |
| 8 | 0.27 | 0.66 | 0.92 | 1.31 |
| 10 | 0.31 | 0.66 | 0.90 | 1.33 |
| 15 | 0.32 | 0.68 | 0.94 | 1.29 |
| 20 | 0.31 | 0.70 | 0.93 | 1.31 |
| 30 | 0.30 | 0.69 | 0.94 | 1.29 |

According to this a total T4 test with a good gradation can be realised with DR concentrations in the mixture ranging from 8 to 30 mM.

EXAMPLE 5

Test carrier for the determination of total thyroxine (T4)

1. Construction and function of the test carrier

The construction and function of the test carrier corresponds to FIG. 1. In order to be able to detect the total thyroxine present in the serum it is necessary to release the protein-bound T4 by a suitable displacing reagent which is located in the first reagent layer 8.

2. Preparation of the separation layer 13

2.1 Amino-silanisation of $TiO_2$ ($TiO_2$-Si) 50 g $TiO_2$ (RN43, Kronos-Titan, Leverkusen, German Federal Republic (FRG)) is suspended in 1000 ml redistilled water and stirred for 2 hours at 75° C. with 10 ml 3-aminopropyl-triethoxysilane (Sigma-Chemie, Deisenhofen, GFR) while monitoring the pH (pH 3–4). Afterwards it is aspirated over a glass filter (G5) and washed with redistilled water until the pH becomes neutral.

2.2 Synthesis of the bridging molecules ($TiO_2$-Si-GA-Cc)

50 g silanized titanium dioxide ($TiO_2$-Si) is suspended in 250 ml glutardialdehyde solution (25% in water, Sigma-Chemie, Deisenhofen, GFR) and stirred for 12 hours at pH 7.4. Afterwards it is aspirated over a glass filter (G5) and then washed first with redistilled water and subsequently with 0.5M phosphate buffer (pH 7.6). The solid phase is taken up in 225 ml phosphate buffer and stirred for 12 hours with 25 ml crotein-C solution (10% in phosphate buffer, Crotein C from Croda, Nettetal, GFR). In order to saturate any remaining free aldehyde groups, 50 g of the solid phase washed in phosphate buffer is stirred in 500 ml 0.5M phosphate buffer containing 0.5M glycine for 1 hour. After washing intensively (redistilled water) the sediment (ca. 50 g) is taken up in 450 ml borate buffer (pH 8.5) and stirred with 50 ml sodium cyanoborohydride solution (5% in borate buffer) for 15 minutes to reduce the Schiff's bases. Subsequently it is aspirated over a glass filter (G5) and washed with phosphate buffer and redistilled water.

2.3 Coupling of BOC-T4-hydroxysuccinimide ($TiO_2$-Si-GA-Cc-T4) as the analyte analogue 10 g $TiO_2$-Si-GA-Cc is suspended in 200 ml 0.06M $Na_2HPO_4$ (pH 8.8) and stirred for 2 hours in the dark with 170 ml BOC-T4-hydroxysuccinimide solution (0.05% in dioxan). Afterwards it is washed with 0.06M $Na_2HPO_4$/dioxan (10:8.5) and then several times with redistilled water and aspirated.

2.4 Film coating on fabric

A coating material with the following composition:

| | |
|---|---|
| Pripiofan 70 D of polymers based on vinylpropionate) (BASF, Ludwigshafen, GFR) | 4 g |
| Brij 35 (a nonionic tenside based on polyethyleneglycol ethers of lauryl alcohol, cetyl alcohol, stearyl alcohol and oleyl alcohol) (Serva, Heidelberg, GFR) 15% solution in Gal buffer | 1 g |
| Polyox WSR 301 soluble, nonionic polyethylenoxides) (Union Carbide, New York, USA) 2.5% in Gal buffer | 5 g |
| $TiO_2$-T4 matrix coupling 40% suspension in Gal buffer | 30 g |
| Kieselguhr MW 25 | 9 g |
| | 49 g | is applied to a fabric PE 812 K[6] (polyester fabric) (Schweizerische Seidengazefabrik, Thal, Switzerland) with a wet film thickness of 350 μ and dried.

3. Preparation of the displacing reagent on the first reagent layer 8

200 mM displacing reagent (2,2'-dihydroxy-4,4'-dimethoxy-diphenylmethane-5,5'-disulfonic acid (disodium salt)) is dissolved in Gal buffer and impregnated on tea bag paper (Schöller and Hösch, Gernsheim, GFR).

| Gal buffer: | $KH_2PO_4$ | 10 mm |
|---|---|---|
| | $MgCl_2$ | 5 mM |
| | NaCl | 25 mM |
| | pH | 7.0 |

4. Preparation of the second reagent layer 9 as the conjugate layer

The following solution is impregnated on the fabric PE 14 100 (polyester fabric) normal (Schweizer Seidengazefabrik, Thal, Switzerland)

| Composition of the impregnation solution | |
|---|---|
| Hepes | 50 mM |
| $MgCl_2$ | 5 mM |
| Trehalose | 1% |
| Crotein C (hydrolysate of collagen) | 1% |
| <T4>-βGal-conjugate | 80 U/ml |
| pH | 6.6 |

5. Preparation of the third reagent layer 14 as the substrate layer

Impregnation on the fabric PE HD-1 (polyester fabric) (Schweizer Seidengazefabrik, Thal, Switzerland) Composition of the impregnation solution: 20 mM chlorophenol red-galacoside (CPRG) (produced according to EP-A-0 146 866) in Gal buffer.

6. Results

30 μl sera with different total T4 concentrations are applied to test strips and measured in the "Reflotron" instrument of the applicant at 567 nm:

| μg/dl T4 | Reflectance after 1 minute |
|---|---|
| 0.55 | 52.25 |
| 6.65 | 44.51 |
| 10.00 | 38.52 |
| 20.90 | 31.48 |

The gradation which can be achieved in the clinically relevant range of 2.0–17.0 μg/dl allows a very good accuracy of the measurement.

EXAMPLE 6

Influence on the enzymatic activity of β-galactosidase as the enzyme marker by displacing reagents A) Test procedure
The following are pipetted successively into a centrifuge tube:
80 μl serum with 5 μg/dl T4
20 μl displacing reagent solution in buffer (0–40 mM)
Then mix for 2 minutes. Subsequently
25 μl (anti-T4 antibody)-β-galactosidase conjugate in buffer (40 U/ml) is added to this mixture. The buffer is the same as for the displacing reagent. It is mixed again for 2 minutes. Then
20 μl of this mixture is added to
750 μl chlorophenol red-galactoside in buffer (1 mM). Chlorophenol red-galactoside is prepared according to EP-A 0 146 866.
After a short mixing the absorbance change/minute is measured at 578 nm.

In each case the buffer used is an aqueous solution (pH=7.0) of the following substances:
$KH_2PO_4$ 10 mM
$MgCl_2$ 5 mM
NaCl 25 mM B) Results a) Table 3 shows the dependence of the measurement signal (absorbance change per minute) as a measure of the enzymatic activity on the concentration of the displacing reagent (DR) used for the substances 2-hydroxy-4-methoxydiphenylmethane-5-sulfonic acid (sodium salt) (α) (cf. Example 1), 2,2'-dihydroxy-4,4'-dimethoxydiphenylmethane-5,5'-disulfonic acid (disodium salt) (β) (cf. Example 2) and 2-hydroxy-4-methoxybenzophenone-5-sulfonic acid (γ) (state of the art of. EP-A-0 133464).

TABLE 3

| DR concentration in the mixture (mM) | Change in absorbance/minute for substance | | |
|---|---|---|---|
| | α | β | γ |
| 0 | 1.32 | 1.47 | 1.37 |
| 2 | 1.51 | 1.39 | 1.59 |
| 5 | 1.42 | 1.32 | 1.58 |
| 10 | 1.54 | 1.45 | 1.38 |
| 20 | 1.37 | 1.32 | 1.18 |
| 40 | 1.45 | 1.34 | 1.05 |

While the substances (α, β) according to the present invention show no influence on the β-galactosidase activity, the enzymatic activity is substantially influenced by the displacing reagent of the prior art (γ). At higher DR concentrations the enzyme activity is greatly decreased.

The documents referred to and described herein are hereby incorporated by reference for the teachings contained therein. In particular, M. Oellerich, J. Clin. Chem. Clin. Biochem 22 895–904 (1984) is incorporated herein by reference for its teaching of enzyme-immunoassays. EP-A-0 318 777 is incorporated herein by reference for its teaching of a test carrier as shown in FIG. 1, for inorganic carrier particles and for materials comprising the individual layers of a test carrier. EP-A-0 129 220 is incorporated herein by reference for its teaching of applying mechanical pressure to layers of a test carrier.

We claim:

1. A method for the determination of iodothyronine in the presence of iodothyronine-binding protein which is not an antibody, in a liquid sample comprising the steps of:

adding a substance which displaces and releases protein-bound iodothyronine, said substance being a compound of the formula I

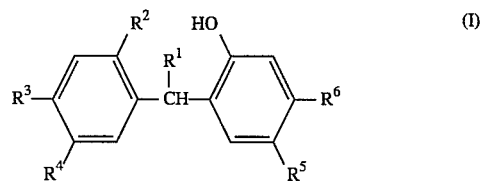

wherein $R^1$ is hydrogen or hydroxy, $R^2$ is hydrogen or hydroxy, $R^3$ is hydrogen or alkoxy, $R^4$ is hydrogen or is selected from the group consisting of $SO_3H$, and a salt thereof, $R^5$ is selected from the group consisting of $SO_3H$, and a salt thereof, $R^6$ is alkoxy, and determining the total iodothyronine in the sample.

2. The method according to claim 1, wherein the determination of the total iodothyronine in the sample is accomplished by means of an immunological method.

3. The method according to claim 1, wherein said substance which displaces and releases protein bound iodothyronine is selected from the group consisting of 2-hydroxy-4-methoxydiphenylmethane-5-sulfonic acid, and 2,2'-dihydroxy-4,4'dimethoxydiphenylmethane-5,5'-disulfonic acid and sodium salts thereof.

4. A reagent for the determination of iodothyronine in a sample, comprising a substance which displaces iodothyronine from a protein which binds iodothyronine, wherein said protein is not an antibody, and wherein said substance is of the formula I

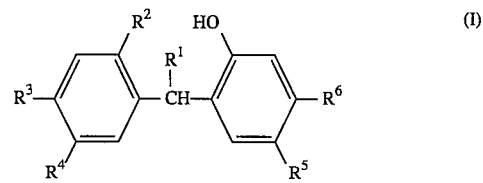

wherein $R^1$ is hydrogen, $R^2$ is hydrogen or hydroxy, $R^3$ is hydrogen or alkoxy, $R^4$ is hydrogen or is selected from the group consisting of $SO_3H$ and a salt thereof, $R^5$ is selected from the group consisting of $SO_3H$ and a salt thereof, R⁶ is alkoxy, and an agent which generates a signal which represents the amount of free unbound iodothyronine in the sample.

5. The reagent according to claim 4, wherein the substance for displacing iodothyronine from a protein which binds iodothyronine is not mixed together with the agent which generates a signal.

6. The reagent according to claim 4, wherein the substance for displacing iodothyronine from a protein which binds iodothyronine is readily soluble in water and wherein said substance is initially present in or on a solid carrier.

7. The reagent according to claim 4, wherein the substance for displacing iodothyronine from a protein which binds iodothyronine is readily soluble in water and Wherein said substance is initially impregnated in a carrier.

8. The reagent according to claim 4, wherein said substance which displaces iodothyronine is selected from the group consisting of 2-hydroxy-4-methoxydiphenylmethane-5-sulfonic acid, and 2,2'-dihydroxy-4,4'dimethoxydiphenyl-methane-5,5'-disulfonic acid and sodium salts thereof.

9. A method for determining the presence of iodothyronine in a liquid sample containing iodothyronine-binding protein which is not an antibody, comprising the steps of:

adding an iodothyronine separating agent to said sample to separate iodothyronine from said iodothyronine-binding protein, said separating agent being of the formula I

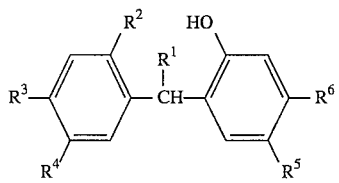

wherein R· is hydrogen or hydroxy,

R² is hydrogen or hydroxy,

R³ is hydrogen or alkoxy,

R⁴ is hydrogen or is selected from the group consisting of SO₃H, and a salt thereof, R⁵ is selected from the group consisting of SO₃H, and a salt thereof, R⁶ is alkoxy, adding a labeled antibody which binds to the unbound iodothyronine in said liquid sample;

separating labeled antibody not bound to iodothyronine from antibody bound to iodothyronine by immobilizing said antibody not bound to iodothyronine on a solid phase;

separating said solid phase from said liquid sample; and measuring the amount of iodothyronine present in said liquid sample.

10. The method according to claim 9, wherein the measuring of the amount of iodothyronine in said liquid sample is accomplished by adding a substrate to said liquid sample which reacts with said label to produce a detectable signal.

11. The method according to claim 9, wherein said solid phase comprises a carrier and iodothyronine bound thereto.

12. The method according to claim 9, wherein said iodothyronine separating agent is selected from the group consisting of 2-hydroxy-4-methoxydiphenylmethane-5-sulfonic acid, and 2,2'-dihydroxy-4,4'dimethoxydiphenyl-methane-5,5'-disulfonic acid and sodium salts thereof.

13. A method for determining the presence of iodothyronine in a liquid sample containing iodothyronine-binding protein which is not an antibody, comprising the steps of:

adding an iodothyronine separating agent to said sample to separate iodothyronine from said iodothyronine-binding protein, said separating agent being of the formula I

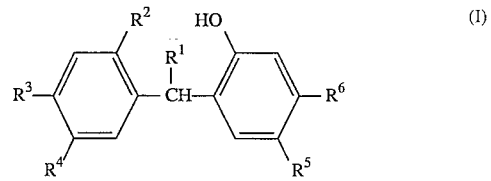

wherein R¹ is hydrogen or hydroxy,

R² is hydrogen or hydroxy,

R³ is hydrogen or alkoxy,

R⁴ is hydrogen or is selected from the group consisting of SO₃H, and a salt thereof, R⁵ is selected from the group consisting of SO₃H, and a salt thereof, R⁶ is alkoxy, adding an enzymatically labeled antibody which binds to the unbound iodothyronine in said liquid sample;

separating labeled antibody not bound to iodothyronine from antibody bound to iodothyronine by immobilizing said antibody not bound to iodothyronine on a solid phase;

separating said solid phase from said liquid sample; and measuring the amount of label present in said solid phase as an indication of the amount of iodothyronine in the sample.

14. The method according to claim 13, wherein the measuring of the amount of label in said solid phase is accomplished by adding a substrate to said solid phase which reacts with said label to produce a detectable signal.

15. The method according to claim 13, wherein said iodothyronine separating agent is selected from the group consisting of 2-hydroxy-4-methoxydiphenylmethane-5-sulfonic acid, and 2,2'-dihydroxy-4,4'dimethoxydiphenyl-methane-5,5'-disulfonic acid and sodium salts thereof.

16. A method for separating iodothyronine from an iodothyronine binding protein which is not an antibody, comprising contacting a protein having iodothyronine bound thereto with an iodothyronine separating agent of the formula I

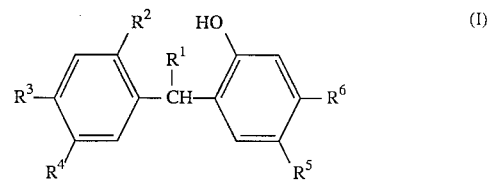

wherein R¹ is hydrogen or hydroxy,

R² is hydrogen or hydroxy,

R³ is hydrogen or alkoxy,

R⁴ is hydrogen or is selected from the group consisting of SO₃H, and a salt thereof, R⁵ is selected from the group consisting of SO₃H, and a salt thereof, and R⁶ is alkoxy.

17. The method according to claim 16, wherein R¹ is hydrogen.

18. The method according to claim 16, wherein said iodothyronine separating agent is selected from the group consisting of 2-hydroxy-4-methoxydiphenylmethane-5-sulfonic acid, and 2,2'-dihydroxy-4,4'dimethoxydiphenylmethane-5-540 -disulfonic acid and sodium salts thereof.

19. A method for separating iodothyronine from a protein which binds iodothyronine, wherein said protein is not an antibody, comprising contacting a protein having iodothyronine bound thereto with an iodothyronine separating agent of the formula I

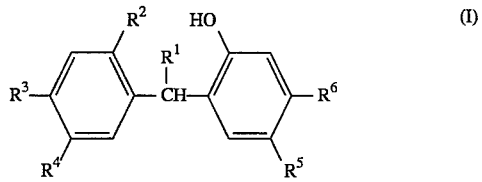

(I)

wherein $R^1$ is hydrogen or hydroxy, $R^2$, $R^3$ and $R^4$ are hydrogen, $R^5$ is selected from the group consisting of $SO_3H$ and a salt thereof, and $R^6$ is alkoxy.

20. A method for separating iodothyronine from a protein which binds iodothyronine, wherein said protein is not an antibody, comprising contacting a protein having iodothyronine bound thereto with an iodothyronine separating agent of the formula I

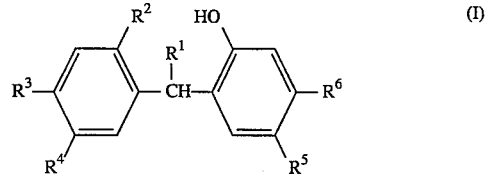

(I)

wherein $R^1$ is hydrogen or hydroxy, $R^2$ is hydroxy, $R^3$ is alkoxy, $R^4$ is selected from the group consisting of $SO_3H$ and a salt thereof, $R^5$ is selected from the group consisting of $SO_3H$ and a salt thereof, and $R^6$ is alkoxy.

* * * * *